United States Patent
Lippitz et al.

(10) Patent No.: US 9,709,638 B2
(45) Date of Patent: Jul. 18, 2017

(54) IMPLANT WITH MRI DEVICE RECOGNITION

(71) Applicant: Biotronik SE & Co. KG, Berlin (DE)

(72) Inventors: Holger Lippitz, Berlin (DE); Ingo Weiss, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 108 days.

(21) Appl. No.: 14/803,014

(22) Filed: Jul. 17, 2015

(65) Prior Publication Data
US 2016/0061911 A1 Mar. 3, 2016

Related U.S. Application Data

(60) Provisional application No. 62/044,339, filed on Sep. 1, 2014.

(51) Int. Cl.
| | | |
|---|---|---|
| *A61N 1/08* | (2006.01) | |
| *G01R 33/032* | (2006.01) | |
| *A61N 1/37* | (2006.01) | |
| *A61B 5/00* | (2006.01) | |
| *A61B 5/055* | (2006.01) | |
| *G01R 33/28* | (2006.01) | |
| *A61B 19/00* | (2006.01) | |

(52) U.S. Cl.
CPC ........ *G01R 33/0322* (2013.01); *A61B 5/0031* (2013.01); *A61B 5/055* (2013.01); *A61N 1/08* (2013.01); *A61N 1/3718* (2013.01); *A61B 2019/5445* (2013.01); *G01R 33/285* (2013.01); *G01R 33/288* (2013.01)

(58) Field of Classification Search
CPC  G01R 33/0322; G01R 33/285; G01R 33/288; A61B 5/0031; A61B 5/055; A61B 2019/5455; A61N 1/08; A61N 1/3718
USPC ..... 607/63, 62, 27, 11, 6; 600/421, 422, 407
See application file for complete search history.

(56) References Cited

U.S. PATENT DOCUMENTS

| | | | |
|---|---|---|---|
| 6,307,367 | B1 | 10/2001 | Heid |
| 6,462,539 | B2 * | 10/2002 | Moriya .............. G01R 33/0322 324/244.1 |
| 2006/0247702 | A1 | 11/2006 | Stegemann et al. |
| 2008/0154342 | A1 | 6/2008 | Digby et al. |

(Continued)

FOREIGN PATENT DOCUMENTS

| | | |
|---|---|---|
| DE | 19920429 A1 | 11/2000 |
| EP | 0793975 A2 | 9/1997 |

(Continued)

OTHER PUBLICATIONS

European Search Report received from EP Application Serial No. 16166557.5, dated Nov. 11, 2016, 8 pages.

(Continued)

*Primary Examiner* — Michael Carey
(74) *Attorney, Agent, or Firm* — Arc IP Law, PC; Joseph J. Mayo

(57) ABSTRACT

An implant with magnetic field recognition, such as an implant that recognizes fields generated by a magnetic resonance imaging (MRI) device. The implant includes at least one voltage source, at least one control unit, at least one communication coil and an optical structure with a Faraday element. The optical structure includes at least one first and second polarization filters and at least one light detector.

15 Claims, 3 Drawing Sheets

(56) References Cited

U.S. PATENT DOCUMENTS

| | | |
|---|---|---|
| 2010/0022856 A1 | 1/2010 | Cinbis et al. |
| 2010/0030043 A1 | 2/2010 | Kuhn |
| 2010/0087892 A1 | 4/2010 | Stubbs et al. |
| 2010/0280348 A1 | 11/2010 | Wenzel et al. |
| 2011/0009754 A1 | 1/2011 | Wenzel et al. |
| 2011/0152667 A1 | 6/2011 | Doerr et al. |
| 2011/0152672 A1* | 6/2011 | Doerr ................. A61N 1/37 600/421 |

FOREIGN PATENT DOCUMENTS

| | | |
|---|---|---|
| EP | 2338559 A1 | 6/2011 |
| EP | 2338564 A2 | 6/2011 |
| WO | 2013055246 A2 | 4/2013 |

OTHER PUBLICATIONS

European Search Report received from EP Application Serial No. 15173598.2, dated Feb. 3, 2016, 5 pages.

\* cited by examiner

IMPLANT WITH MRI DEVICE RECOGNITION

This application claims the benefit of U.S. Provisional Patent Application 62/044,339 filed on 1 Sep. 2014, the specification of which is hereby incorporated herein by reference.

BACKGROUND OF THE INVENTION

Field of the Invention

Embodiments of the invention generally relate to an implant with magnetic field recognition, specifically an implant that recognizes fields that are generated by a magnetic resonance imaging (MRI) device.

Description of the Related Art

Although examinations with magnetic resonance imaging (MRI) devices are generally developing an increasingly more significant role in diagnostic medicine, these examinations with MRI devices are contraindicated for a significant proportion of potential patients. Typically, such a contraindication can be caused for example by the presence of an implanted medical device (IMD).

Generally, there are various approaches for increasing the compatibility of implanted medical devices with MRI devices, more specifically with the working conditions in the field of influence of an MRI device. As such, typically, it is attempted to detect the fields that are characteristic for MRI devices so as to draw corresponding conclusions therefrom.

Generally, various methods for detecting magnetic fields and other electromagnetic fields are known from the prior art.

For example, United States Patent Publication 20080154342 to Digby et al., entitled "Implantable Medical Device Comprising Magnetic Field Detector", appears to describe a magnetic field detector based on a giant magnetoresistance (GMR) sensor or a band-pass filter in the antenna circuit.

In addition, for example, United States Patent Publication 20110152672, patented as U.S. Pat. No. 8,781,588, to Doerr et al., entitled "MRT Optocoupler", describes an implant in which an electro-optical transducer is used to detect radio frequency (RF) and high frequency (HF) fields typical for MRI devices.

Furthermore, for example, U.S. Pat. No. 6,462,539 to Moriya et al., entitled "Magnetic Sensor with Faraday Element", appears to disclose an apparatus that determines magnetic fields using an optical structure with a birefringence element, which is based on the Faraday effect.

The described prior art generally relate to a measurement of a static magnetic field or the measurement of typical RF/HF fields, or a combination of two measurement methods to determine both the static magnetic fields and the HF fields; wherein the term HF, hereinafter, will also include RF. A simultaneous detection of the RF/HF fields and the magnetic fields in one measuring unit is not previously known. Typically, the previous optical superstructures also have to be calibrated in a complex manner for quantitative statements or require a complex structure.

BRIEF SUMMARY OF THE INVENTION

One or more embodiments of the invention provide an implant and a measuring system thereof to overcome the deficiencies in the prior art as discussed above.

At least one embodiment of the invention includes a device, such as an implantable medical device (IMD). In one or more embodiments, the IMD may include one or more of at least one voltage source, at least one control unit, at least one communication coil, and an optical structure.

In at least one embodiment, the optical structure may include one or more of at least one light-emitting diode (LED), at least one light detector, at least one first polarization filter and at least one second polarization filter, and at least one optical fiber. In one or more embodiments, the optical fiber may be formed as, or may include, a Faraday element. In at least one embodiment, the optical structure may include at least one optical path.

By way of one or more embodiments, the at least one LED may be electronically connected to the at least one communication coil such that the at least one LED emits light when a high frequency (HF) field is coupled into the at least one communication coil. In at least one embodiment, the at least one LED may be connected to a first side of the at least one first polarization filter, and a second side of the at least one first polarization filter may be connected to a first end of the Faraday element. In one or more embodiments, a first side of the at least one second polarization filter may be connected to a second end of the Faraday element, and a second side of the at least one second polarization filter may be connected to the at least one light detector. By way of at least one embodiment, the Faraday element may include at least one bend and the Faraday element may be divided by the at least one bend into at least two portions. In one or more embodiments, the Faraday element may be fixedly anchored in a molded article via a bend corresponding to the at least one bend of the Faraday element.

According to at least one embodiment, the Faraday element may be one or more of inlaid in a molded article, connected to the molded article, and surrounded, for example cast around, in a predefined mold by a material forming a solid. Due to the bend, in one or more embodiments, the Faraday element is sensitive to magnetic fields in a plane, and as such the static magnetic field of an MRI device may be detected. In at least one embodiment, the magnetic field may be determined only in the plane spanned by the Faraday element.

In one or more embodiments, the light detected by the at least one light detector may be evaluated by an evaluation unit or evaluation device and may generate a corresponding control signal, which causes a switchover or maintenance of an operating mode of the implanted medical device (IMD). In at least one embodiment, the described HF field, which may be coupled into or may influence the communication coil, may include an RF field, such as an RF signal of an MRI device, wherein the frequency of the RF signal is dependent on the magnetic flux density of the MRI device.

In one or more embodiments, the at least one bend may include an angle of 90° between each of the at least two portions of the Faraday element. In at least one embodiment, the angle may include another value in adaptation to the implantable medical implant, such as an angle adapted to the shape of the housing of the IMD. By way of one or more embodiments, the radius of curvature may be adapted to the radius of curvature of the housing of the implantable medical device. In at least one embodiment, with the presence of more than one bend, only one angle may be 90°, or a number of angles, but not all, may be 90°. In one or more embodiments, the at least two bends may be formed such that the Faraday element includes a longitudinal extent or extension in all three spatial directions, and such that a magnetic field determination is possible not just in one plane, but in the entire triad, or space, spanned by all of the three spatial directions. By way of at least one embodiment, the implants may extend little in one spatial direction, for example may be flat. In one or more embodiments, a number of portions of the Faraday element may run in the one spatial direction, for example to lay the Faraday element in a zigzagged or meandering manner in the one spatial direction, in order to provide a sufficient path to detect the occurrence of the Faraday effect.

In at least one embodiment, the optical structure may be integrated in a mounting frame, wherein the molded article may be wholly or partially part of a mounting frame. In one or more embodiments, the molded article may be incorporated wholly or partially into the mounting frame and may be part of the mounting frame.

In at least one embodiment, the at least one first and the at least one second polarization filters may be set such that, without the presence of a magnetic field, no light exits through the at least one second polarization filter and no light impinges on the at least one light detector. In one or more embodiments, the polarization filters may be in a crossed manner. In at least one embodiment, the optical elements used may influence the polarization direction of the light, even without the presence of a magnetic field. As such, by way of one or more embodiments, the influence thereof may be compensated for with the structure. In at least one embodiment, the angle between the polarization directions of the at least one first and the at least one second polarization filters may deviate from 90 degrees. According to one or more embodiments, the angle may vary from structure to structure. At least one embodiment of the invention may include the property that no light or only a minimal amount of light exits from the second polarization filter, wherein the at least one first and the at least one second polarization filters may be arranged in crossed form, when no magnetic field acts on the structure.

In at least one embodiment, the molded article may be made of or may include a light-impermeable material, and the molded article may surrounds the Faraday element, such that light may enter the Faraday element only through the two sides associated with the at least one first and the at least one second polarization filters. In one or more embodiments, the structure of the molded article and the Faraday element may reduce stray light, which leads to increased background noise. As such, in at least one embodiment, the sensitivity and accuracy of the magnetic field determination is increased.

In one or more embodiments, the entire optical structure may be cast around with a light-impermeable plastic such that no stray light may be coupled into the optical structure. As with the molded article made of a light-impermeable material, in at least one embodiment, stray light may be minimized in the optical structure. One or more embodiments of the invention may include both measures of stray light reduction combined.

In at least one embodiment, the Faraday element may include a Verdet constant of at least 2 radians per tesla per meter in the range of the light spectrum emitted by the at least one LED or part of the light spectrum emitted by the at least one LED.

In one or more embodiments, the Faraday element may include a glass fiber. In at least one embodiment, the Faraday element may be formed from, or may include, a tempered glass fiber, such as a glass fiber held at elevated temperature and cooled slowly. In one or more embodiments, the tempering process may be performed when the glass fiber has already been brought into the subsequently desired form, for example with respect to the bend or the bends.

In at least one embodiment, the Faraday element may include at least one further bend, such that the Faraday element may detect a magnetic field in all three spatial directions. By way of one or more embodiment, the then at least three Faraday element portions may be formed as an orthogonal triad. In at least one embodiment, one spatial extension or direction in the implantable medical device may be much shorter than in the other two spatial directions or extensions, for example similarly to a flat cuboid. In one or more embodiments, the Faraday element may be passed back and forth at least once, or a number of times, in the shorter spatial direction, such that the total length in the shorter spatial direction corresponds approximately to the length in the other spatial directions.

By way of at least one embodiment, the at least one light detector may be connected to an evaluation unit or evaluation device which determines, on the basis of the intensity change of the detected light, whether the magnetic field present includes a magnetic flux density less than or equal to 1 tesla, or 1.5 tesla or 5 tesla or 7 tesla.

According to one or more embodiments, the evaluation unit or device may generate a control signal depending on the determined magnetic field strength or the magnetic flux density. In at least one embodiment, the implanted medical device with the evaluation unit or device may draw different conclusions from the light detected. For example, in one or more embodiments, different operating modes of the implanted medical device may be initiated by different detection results.

At least one embodiment may include a second optical path, also referred to herein as a further optical path, that leads from the at least one LED to the at least one light detector or a further light detector, wherein the further optical path may be used as a reference without being influenced by a magnetic field. In one or more embodiments, the further optical path may be produced by, or may include, for example, an optical fiber having a very low Verdet constant in the range of the light spectrum emitted by the at least one LED or part of the light spectrum emitted by the at least one LED.

By way of at least one embodiment, the further optical path may lead to a further light detector, and the light detectors may be connected to an evaluation unit or device that determines, on the basis of the intensity change of the detected light, whether the magnetic field present has a magnetic flux density less than or equal to 1 tesla, or 1.5 tesla or 3 tesla or 7 tesla. In one or more embodiments, the evaluation unit or device may use the further optical path as a reference path to determine the magnetic field strength or the magnetic flux density.

In at least one embodiment, the at least one LED may be connected to the voltage source or a further voltage source such that even a lower HF coupling, than without the connection to the voltage source or the further voltage source, is sufficient for the at least one LED to emit light. As such, one or more embodiments may be more sensitive to the HF fields. As such, in at least one embodiment, the luminous efficacy may be increased and therefore the measurement inaccuracy is reduced.

By way of one or more embodiments, the at least one LED may be protected by a current limiter. As such, in at least one embodiment, a limitation of the maximum light intensity may be achieved, wherein a calibration of the system to determine the magnetic field strength or the magnetic flux density is possible. In one or more embodiments, the calibration of the system may occur when the HF fields induced in the communication coil are likewise evaluated and included by the evaluation unit or device in the magnetic field determination. In at least one embodiment, the term "magnetic field determination" described herein relates to the magnetic flux density in tesla, wherein tesla corresponds with the specification of MRI devices.

In one or more embodiments, the bias at the at least one LED may be below the opening limit of the at least one LED.

In at least one embodiment, the at least one LED may be decoupled from direct current components by at least one capacitor on at least one side.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
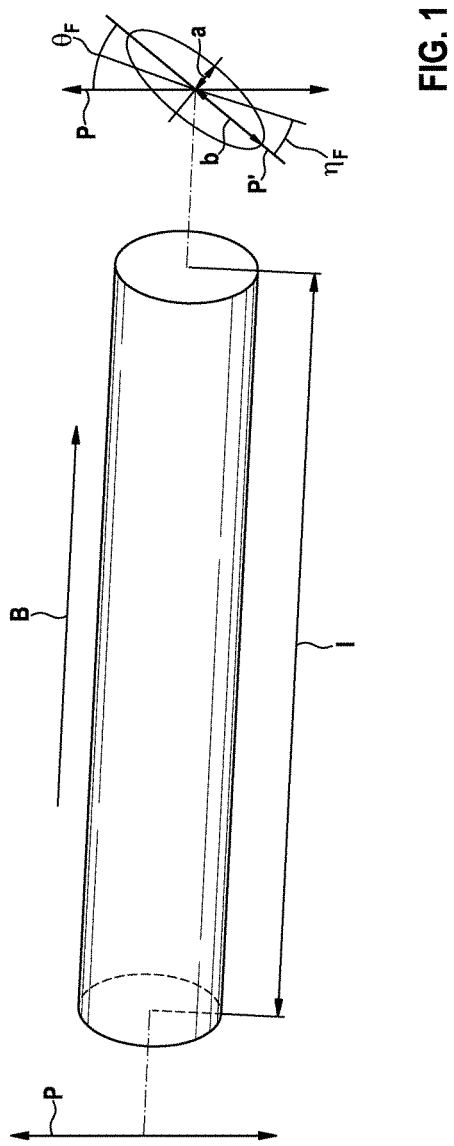
FIG. 1 schematically shows the Faraday effect.

FIG. 1 schematically shows the operating principle of a Faraday element, wherein P is the original polarization direction, B is the direction of the magnetic field, l is the length of the Faraday element, P' is the resultant polarization direction, a and b are the large and small half-axis of the resultant ellipsoids, theta F is the Faraday rotation or the angle of rotation of the polarization, and eta F is the Faraday ellipticity, according to one or more embodiments of the invention.

Figure 2:
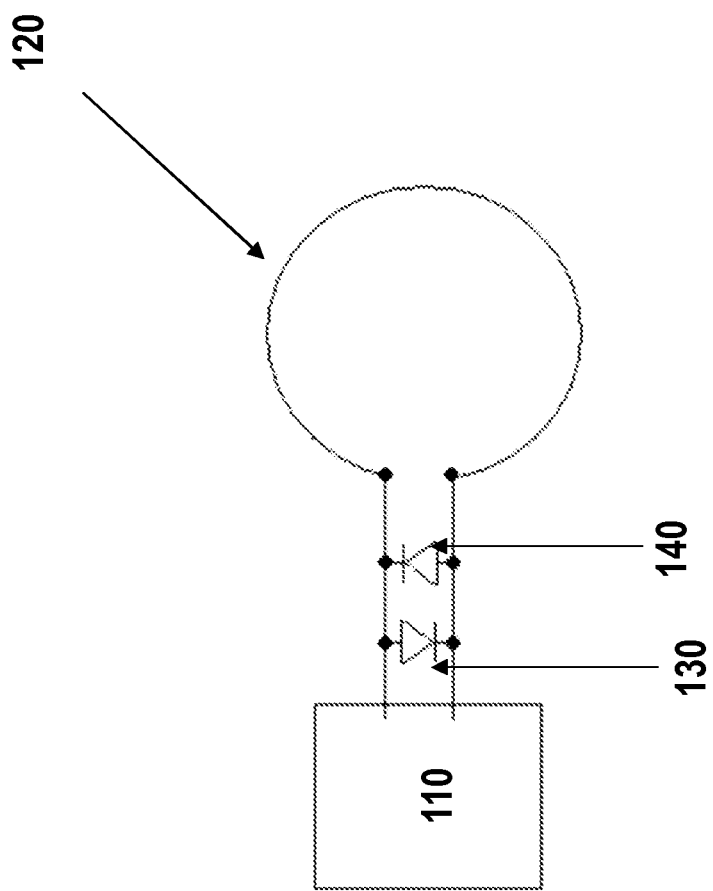
FIG. 2 shows a communication coil with two light-emitting diodes and a control unit.

FIG. 2 shows part of a circuit diagram of an implant that includes a voltage source, a control unit 110 and a communication coil 120, according to one or more embodiments of the invention. In at least one embodiment, the control unit 110 may be electrically connected via at least one LED, such as via two LEDs 130, 140, to the communication coil, such that the at least one LED emits light when an HF field of MRI devices is coupled in via the communication coil 120. In one or more embodiments, the control unit 110 may connect the communication coil 110 to other components of the implantable medical implant.

Figure 3:
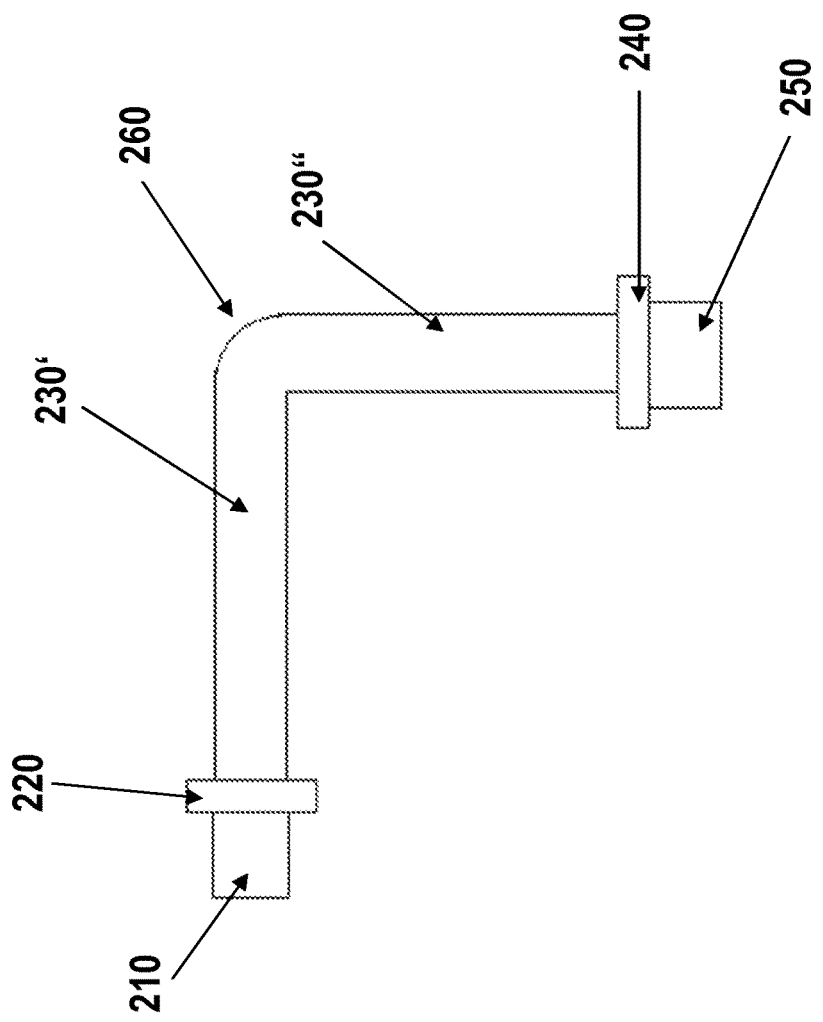
FIG. 3 shows an optical structure with a bend, according to one or more embodiments of the invention.

FIG. 3 schematically shows the optical structure according to one or more embodiments of the invention. As shown in FIG. 3, one or more embodiments may include at least one LED 210 that may be connected via an optical structure to a light detector 250, for example a photodiode. By way of at least one embodiment, the optical structure may include one or more other components including at least one first polarization filter 220, and at least one Faraday element 230', 230", for example a doped glass rod with high Verdet constant or a glass fiber with high Verdet constant. In one or more embodiments, the at least one Faraday element 230', 230" may include a glass fiber with maintained polarization under bending and with a high Verdet constant, for example a tempered glass fiber. In at least one embodiment, the Faraday element 230', 230" may be adjoined by a further or at least one second polarization filter 240, which is rotated by 90° relative to the at least one first polarization filter, such that the at least one second polarization filter 240 crosses the at least one first polarization filter 220. One or more embodiments may include a glass fiber. In at least one embodiment, the glass fiber may not run in a straight line, wherein the glass fiber may already cause a rotation of the polarization direction or a depolarization without the presence of a magnetic field, such that the angle between the polarization filters may deviate from 90° in order to prevent the passage of the light through the at least one second polarization filter 240. By way of at least one embodiment, the light detector 250 may be connected to the control unit 110 or to an evaluation unit or device, and wherein the light detector 250 may be connected to the voltage source or a further voltage source by the control unit 110 or by the evaluation unit or directly. In one or more embodiments, the light detector 250 may send a signal to the control unit 110 when the light detector 250 detects light above a predetermined intensity. By way of at least one embodiment, the signal may be a constant signal or may be dependent on the detected intensity. In one or more embodiments, the evaluation unit may read out a voltage and/or a current signal from the light detector 250 and may process the voltage and/or the current signal further or transmit the voltage and/or the current signal to the control unit 110.

One or more embodiments may include a Verdet constant of 5.7 rad*T-1 m-1 for SiO2 at 2.27 eV and a length of a glass fiber as Faraday element 230', 230" of 5 cm and a magnetic field strength of 1 tesla. As such, with such values, at least one embodiment may include a Faraday rotation of approximately 16°, wherein the polarization axis of the light is inclined by 16° as the light passes through the glass fiber in a magnetic field with the strength of one tesla, wherein the polarization filters 220, 240 may no longer be crossed under these conditions for the light, and wherein a component of the light may pass through the second polarization filter 240 and may be detected on the light detector 250.

In order to prevent stray light from being coupled into the optical structure, by way of one or more embodiment, the structure may include a housing, such as a housing that may be integrated wholly or partially in a mounting frame or may be part of such a mounting frame wholly or partially.

In order to form the optical structure in a manner that is as stable as possible, in at least one embodiment, the elements of the optical structure, such as the LEDs, the polarization filters, the Faraday element and the photodetector, may be fixedly connected in a component to be immovable relative to one another. In one or more embodiments, the components of the optical structure may be cast in a plastic or cast around with a plastic.

FIG. 3 shows an example of a Faraday element 230', 230", according to one or more embodiments of the invention, wherein the Faraday element 230', 230" may include a bend 260 of 90°. In at least one embodiment, the Faraday element 230', 230" may be divided into two regions 230' and 230", wherein each region 230' and 230" may be sensitive to another component of the magnetic field in a plane. As such, in one or more embodiments, the magnetic field may be detected, irrespective of the position thereof, in the plane spanned by the two Faraday element portions.

In at least one embodiment, the plane spanned by the two Faraday elements 230', 230" may be parallel to the housing side of the implant having the greatest area.

In one or more embodiments, the two Faraday element portions 230', 230" may be produced by, or may include, a glass fiber that includes a bend 260. In at least one embodiment, the polarization filters may be rotated relative to one another such that no light may pass through the second polarization filter 240 without the presence of a magnetic field.

One ore more embodiments of the invention may include three Faraday element portions, wherein the three Faraday element portions may span a space and may detect magnetic fields in all three spatial directions. For example, in at least one embodiment, the three Faraday element portions may be produced by, or may include, a glass fiber having two bends.

In one or more embodiments, the light of the at least one LED 130, 140, 210 may be guided over a further optical path without a Faraday element to a further light detector and may be available or may be used as a reference. In at least one embodiment, the reference may be used to draw conclusions concerning the quantitative rotation of the polarization and therefore the strength of the magnetic field. In one or more embodiments, the intensity of the detected light may be dependent on one hand on the magnitude of the rotation of the polarization, wherein the second polarization filter 240 allows the light to pass with a factor of the sine of the angle of rotation of the polarization. On the other hand, in at least one embodiment, the intensity of the detected light may depend on the magnetic field strength that causes the rotation of the direction of polarization in the Faraday element, wherein the angle of rotation is equal to magnetic field strength in tesla times Verdet constant times path length in the Faraday element parallel to the magnetic field. In one or more embodiments, the attenuation of the light intensity by the used optical components may be taken into consideration. In at least one embodiment, the information concerning the magnetic field strength may be used to distinguish between different MRI device types, such as 1 tesla, 1.5 tesla, 3 tesla, and 7 tesla.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable medical device (IMD) comprising
   at least one voltage source,
   at least one control unit,
   at least one communication coil, and
   an optical structure, wherein the optical structure comprises
      at least one light-emitting diode (LED),
      at least one light detector,
      at least one first and at least one second polarization filters, wherein each of the at least one first and at least one second polarization filters comprise a first side and a second side,
      at least one optical fiber, wherein the at least one optical fiber is formed as a Faraday element, wherein the Faraday element comprises a first end and a second end, and,
   at least one optical path,
   wherein the at least one LED is electronically connected to the at least one communication coil such that the at least one LED emits light when a first high frequency (HF) field is coupled into the at least one communication coil,
   wherein the at least one LED is connected to the first side of the at least one first polarization filter,
   wherein the second side of the at least one first polarization filter is connected to the first end of the Faraday element,
   wherein the first side of the at least one second polarization filter is connected to the second end of the Faraday element,
   wherein the second side of the at least one second polarization filter is connected to the at least one light detector,
   wherein the Faraday element further comprises at least one bend and wherein the Faraday element is divided by the at least one bend into at least two portions, and
   wherein the Faraday element is fixedly anchored in a molded article via a bend corresponding to the at least one bend of the Faraday element.

2. The IMD as claimed in claim 1, wherein the at least one bend produces an angle between the at least two portions of the Faraday element, wherein the angle is 90° in each case.

3. The IMD as claimed in claim 1, wherein the at least one first and the at least one second polarization filters are set such that, without a presence of a magnetic field, no light exits through the at least one second polarization filter and no light impinges on the at least one light detector.

4. The IMD as claimed in claim 1, wherein the molded article comprises a light-impermeable material and wherein the molded article surrounds the Faraday element, such that light enters the Faraday element only through the first and the second sides associated with the at least one first and the at least one second polarization filters.

5. The IMD as claimed in claim 1, wherein the optical structure is entirely cast around with a light-impermeable plastic such that no stray light is coupled into or influences the optical structure.

6. The IMD as claimed in claim 1, wherein the Faraday element has a further comprises a Verdet constant of at least 2 radians per tesla per meter in a range of a light spectrum emitted by the at least one LED or part of the light spectrum emitted by the at least one LED.

7. The IMD as claimed in claim 1, wherein the Faraday element further comprises a glass fiber.

8. The IMD as claimed in claim 1, wherein the Faraday element further comprises at least one second bend, such that the Faraday element detects a magnetic field in all three spatial directions.

9. The IMD as claimed in claim 1, wherein the at least one light detector is connected to an evaluation unit which determines, on the basis of an intensity change of a detected light, whether a magnetic field present comprises a magnetic flux density less than or equal to 1 tesla, or 1.5 tesla or 3 tesla or 7 tesla.

10. The IMD as claimed in claim 9, wherein the evaluation unit generates a control signal depending on the magnetic flux density.

11. The IMD as claimed in claim 1, further comprising a second optical path that leads from the at least one LED to one or more of the at least one light detector and at least one further light detector, wherein the second optical path is configured as a reference path without allowing an intensity of the light emitted by the at least one LED to be influenced by a magnetic field.

12. The IMD as claimed in claim 11, wherein the second optical path leads to the at least one further light detector, wherein the at least one light detector and the at least one further light detector are connected to the at least one evaluation unit, and wherein the at least one evaluation unit determines, on the basis of an intensity change of a detected light, whether the magnetic field present comprises a magnetic flux density less than or equal to 1 tesla, or 1.5 tesla or 3 tesla or 7 tesla.

13. The IMD as claimed in claim 1, wherein the at least one LED is additionally connected to the at least one voltage source or to a further voltage source such that a lower second HF field coupling is sufficient for the at least one LED to emit light without the at least one LED additionally connected to the at least one voltage source or the further voltage source, wherein the lower second HF field coupling is lower than the first HF field coupling.

14. The IMD as claimed in 13, wherein, due to the at least one LED additionally connected to the at least one voltage source or to the further voltage source, a bias is applied across the at least one LED and wherein the bias is below an opening limit of the at least one LED.

15. The IMD as claimed in claim 1, further comprising at least one capacitor and at least one feed line from the at least one communication coil to the at least one LED, wherein the at least one capacitor is on the at least one feed line, and wherein the at least one LED is decoupled from direct current components by at least one capacitor.

* * * * *